United States Patent
Olejnik et al.

(10) Patent No.: US 6,562,873 B2
(45) Date of Patent: *May 13, 2003

(54) COMPOSITIONS CONTAINING THERAPEUTICALLY ACTIVE COMPONENTS HAVING ENHANCED SOLUBILITY

(75) Inventors: Orest Olejnik, Coto de Coza, CA (US); Edward D. S. Kerslake, Charleston, MA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/903,962

(22) Filed: Jul. 10, 2001

(65) Prior Publication Data

US 2002/0071874 A1 Jun. 13, 2002

Related U.S. Application Data

(60) Provisional application No. 60/218,206, filed on Jul. 14, 2000.

(51) Int. Cl.[7] .................... A61K 47/32; A61K 9/00
(52) U.S. Cl. ................... 514/772.4; 514/772.6; 424/400
(58) Field of Search ............ 514/772.4, 772.6; 424/400

(56) References Cited

U.S. PATENT DOCUMENTS

| | | |
|---|---|---|
| 3,278,447 A | 10/1966 | McNicholas |
| 3,890,319 A | 6/1975 | Danielwicz et al. |
| 4,530,920 A | 7/1985 | Nestor et al. |
| 4,806,556 A | 2/1989 | Portoghese |
| 5,021,416 A | 6/1991 | Gluchowski |
| 5,202,128 A | 4/1993 | Morella et al. |
| 5,352,796 A | 10/1994 | Hoeger et al. |
| 5,459,133 A | 10/1995 | Neufeld |
| 5,703,077 A | 12/1997 | Burke et al. |
| 5,719,197 A * | 2/1998 | Kanios et al. ........... 514/772.6 |
| 5,725,887 A | 3/1998 | Martin et al. |
| 5,814,638 A | 9/1998 | Lee et al. |
| 5,834,502 A | 11/1998 | Cheng et al. |
| 5,994,110 A | 11/1999 | Mosbach et al. |

FOREIGN PATENT DOCUMENTS

| | | |
|---|---|---|
| CA | 2048315 | 2/1992 |
| EP | 0609961 | 8/1994 |
| WO | 94/16685 | 8/1994 |
| WO | 98/47878 | 10/1998 |
| WO | 99/43299 | 9/1999 |
| WO | 99/51273 | 10/1999 |
| WO | 0012137 | 3/2000 |
| WO | 0019981 | 4/2000 |

* cited by examiner

Primary Examiner—Thurman K. Page
Assistant Examiner—Blessing Fubara
(74) Attorney, Agent, or Firm—Stout, Uxa, Buyan & Mullins LLP; Frank J. Uxa

(57) ABSTRACT

Compositions which include therapeutically active components, solubility enhancing components other than cyclodextrins, and oxy-chloro components, wherein the oxy-chloro components are substantially effective as preservatives. In one embodiment, the oxy-chloro components are useful for preserving the therapeutically active components. In one embodiment, the oxy-chloro components include chlorite components. In a useful embodiment, the solubility enhancing components include carboxymethylcellulose.

49 Claims, 1 Drawing Sheet

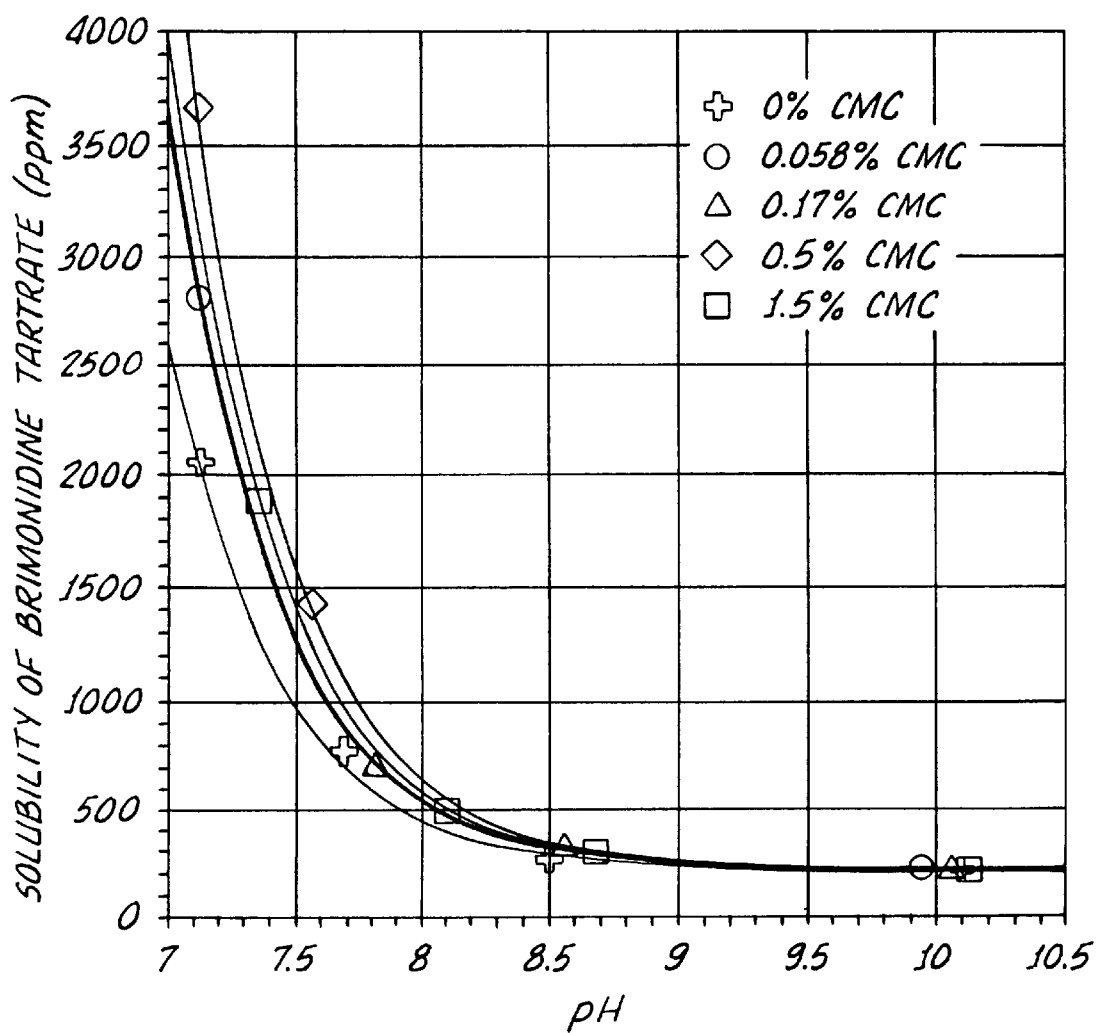

COMPOSITIONS CONTAINING THERAPEUTICALLY ACTIVE COMPONENTS HAVING ENHANCED SOLUBILITY

CROSS REFERENCE TO RELATED APPLICATION

This application claims the benefit of U.S. Provisional Application No. 60/218,206 filed Jul. 14, 2000.

BACKGROUND OF THE INVENTION

The present invention relates to compositions containing therapeutically active components having enhanced solubility. More particularly, the invention relates to compositions which include therapeutically active components (TACs) and components effective to enhance the solubility of the TACs at therapeutically effective concentrations.

TACs in liquid compositions often benefit from being soluble in the liquid carriers of such compositions. Such solubility promotes uniform and accurate administration. Additionally, the dispensed or administered TACs should be soluble in the biological system or environment into which they are administered, for example, for effective or enhanced in vivo diffusion through cell membranes or lipid bilayers. Furthermore, solubilized TACs provide other benefits, for example, reduced irritation to tissues that interact with TACs.

It is sometimes necessary to include solubilizing agents in the compositions to solubilize the TACs. However, the inclusion of solubilizing agents may reduce the effectiveness of the preservatives in the compositions.

For example, cyclodextrins are widely known in the literature to increase the solubility of poorly water soluble therapeutically active components. However, typical preservatives are rendered relatively ineffective by cyclodextrins at normal concentrations in these compositions.

There continues to be a need to provide new compositions containing TACs.

BRIEF SUMMARY OF THE INVENTION

New TAC-containing compositions have been discovered. The present compositions provide for enhanced TAC solubility substantially without detrimentally affecting the effectiveness of the preservative or preservatives being employed. Solubility enhancing components (SECs) have been found which very effectively increase the solubility of the TACs in the present compositions, and preferably in the biological systems or environments into which the components are introduced. Also, preferably, such solubilization allows the provision of more reliable and reproducible dosage forms of the drugs. This solubility enhancement in accordance with the present invention is achieved substantially without degrading preservative effectiveness. In addition, TAC-containing compositions have been discovered which include preservatives which provide substantial advantages, for example, reduced adverse interactions with the TACs and/or with the patients to whom the compositions are administered, while maintaining preservative effectiveness.

The present compositions include oxy-chloro components which are effective in at least assisting in preserving the compositions without detrimentally affecting the TACs and substantially without being detrimentally affected by the SECs. Moreover, the present oxy-chloro components provide preservative action with reduced or even substantially no harm or irritation to the tissues to which the present compositions are administered.

The present SECs preferably are effective in solubilizing the TACs in the environment to which they are introduced, for example, a biological environment. Such solubilization preferably facilitates the advantageous transport of TACs across lipid membranes.

Soluble TACs for use in the present compositions include those components, e.g., compounds, mixtures of compounds, mixtures of other materials, useful to provide a therapeutic benefit or effect when administered to a patient, e.g. a human patient. The TACs useful in this invention include, without limitation, antibacterials, antihistamines, decongestants, antiinflammatories, antiparasitics, miotics, anticholinergics, adrenergics, antivirals, local anesthetics, antifungals, amoebicidals, trichomonocidals, analgesics, mydriatics, antiglaucoma drugs, carbonic anhydrase inhibitors, ophthalmic diagnostic agents, ophthalmic agents used as adjuvants in surgery, chelating agents, antineoplastics, antihypertensives, muscle relaxants, diagnostics and the like and mixtures thereof. Specific examples of such TACs are conventional and well known in the art.

In one embodiment, the TACs include adrenergic agonists, precursors thereof, metabolites thereof and combinations thereof. Preferably, the TACs include alpha-2-adrenergic agonists, for example, imino-imidazolines, imidazolines, imidazoles, azepines, thiazines, oxazolines, guanidines, catecholamines, biologically compatible salts and esters and mixtures thereof. In one embodiment, the TACs include quinoxaline components. Quinoxaline components include quinoxaline, biologically compatible salts thereof, esters thereof, other derivatives thereof and the like, and mixtures thereof. Preferably, the quinoxaline components, including the quinoxaline derivatives, are alpha-2-adrenergic agonists. Non-limiting examples of quinoxaline derivatives include (2-imidazolin-2-ylamino) quinoxaline, 5-bromo-6-(2-imidazolin-2-ylamino) quinoxaline, and biologically compatible salts thereof and esters thereof, preferably the tartrate of 5-bromo-6-(2-imidazolin-2-ylamino) quinoxaline, and the like and mixtures thereof. Hereinafter, the tartrate of 5-bromo-6-(2-imidazolin-2-ylamino) quinoxaline is referred to as "Brimonidine tartrate."

In a useful embodiment, the SEC is other than cyclodextrin and includes a polyanionic component. As used herein, the term "polyanionic component" refers to a chemical entity, for example, an ionically charged species, such as an ionically charged polymeric material, which includes more than one discrete anionic charge, that is multiple discrete anionic charges. Preferably, the polyanionic component is selected from polymeric materials having multiple anionic charges and mixtures thereof.

Particularly useful polyanionic components are selected from anionic polymers derived from acrylic acid (meaning to include polymers from acrylic acid, acrylates and the like and mixtures thereof), anionic polymers derived from methacrylic acid (meaning to include polymers from methacrylic acid, methacrylates, and the like and mixtures thereof), anionic polymers derived from alginic acid (meaning to include alginic acid, alginates, and the like and mixtures thereof), anionic polymers of amino acids (meaning to include polymers of amino acids, amino acid salts, and the like and mixtures thereof), and the like and mixtures thereof. Very useful polyanionic components are those selected from anionic cellulose derivatives and mixtures thereof, especially carboxymethylcelluloses.

The polyanionic component preferably is sufficiently anionic to interact with or otherwise affect, in particular increase, the solubility of the TAC. This interaction preferably is sufficient to render the TAC substantially completely soluble at therapeutically effective concentrations. The amount of SEC in the composition preferably is in the range of about 0.1% (w/v) to about 30% (w/v), more preferably about 0.2% (w/v) to about 10% (w/v), and even more preferably about 0.2% (w/v) to about 0.6% (w/v).

The oxy-chloro components included in the present compositions are effective to at least assist in preserving the compositions. Any suitable oxy-chloro component effective to at least assist in preserving the compositions may be employed. Such oxy-chloro components include, without limitation, hypochlorite components, perchlorate components, chlorite components and the like and mixtures thereof.

In one useful embodiment, the oxy-chloro component includes a chlorite component. Preferably, the chlorite component includes stabilized chlorine dioxides, alkali metal chlorites and the like and mixtures thereof. Chlorite components are very effective in the present compositions and provide preservative effectiveness, often at a relatively reduced concentration, with little or no detrimental effect on the tissue to which the composition is administered. In addition, the oxy-chloro components, e.g., the chlorite components, substantially maintain preservative effectiveness in the presence of the SECs, for example, the polyanionic components. Without wishing to limit the invention to any particular theory or mechanism of operation, it is believed that such oxy-chloro components are substantially free in the presence of the SECs or do not substantially interact the SECs.

The oxy-chloro components may be effective in the compositions in the amount of less than about 1% (w/v) or about 0.8% (w/v). In a useful embodiment, the oxy-chloro components may be in the compositions in the range of about 500 ppm (w/v) or less, preferably about 10 ppm (w/v) to about 200 ppm (w/v).

In one embodiment, additional preservatives other than the oxy-chloro components are used in the compositions. Any suitable additional preservative component may be employed in accordance with the present invention, provided that it is compatible with the oxy-chloro component, the TAC and the SEC. Preservative components which are well known and/or conventionally used in the pharmaceutical field may be employed. Examples include, without limitation, sorbic acids, benzalkonium chlorides, chlorbutols and alkyl esters of p-hydroxybenzoic acids and the like and mixtures thereof. If additional preservative component is included, it preferably is present in an amount, together with the oxy-chloro component, to effectively preserve the composition.

The compositions include a liquid carrier component, for example, an aqueous liquid carrier component. Preferably, the compositions have pH's of about 7 or greater, more preferably about 7 to about 9.

In one broad aspect of the present invention, compositions are provided which comprise a TAC, a SEC, a chlorite component and an aqueous liquid carrier. Preferably the TAC is Brimonidine tartrate. The SEC is preferably an anionic cellulose derivative, more preferably a carboxymethylcellulose, for example, in an amount in the range of about 0.2% to about 0.6% (w/v).

In another broad aspect of the present invention, compositions are provided which comprise a Brimonidine tartrate, a SEC, a chlorite component and an aqueous liquid carrier component. The Brimonidine tartrate is present in an amount effective to provide a desired effect to a human or an animal after the composition is administered to the human or animal, and the SEC is preferably a carboxymethylcellulose.

In another broad aspect of the present invention, compositions are provided which comprise a TAC and a preservative component in an effective amount to at least aid in preserving the compositions. Preferably, the preservative components include oxy-chloro components, such as compounds, ions, complexes and the like which are biologically acceptable, chemically stable and do not substantially or significantly detrimentally affect the TACs in the compositions or the patients to whom the compositions are administered. Such compositions preferably are substantially free of cyclodextrin.

The present compositions preferably are ophthalmically acceptable, e.g. the compositions do not have deleterious or toxic properties which could harm the eye of the human or animal to whom the compositions are administered.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

BRIEF DESCRIPTION OF THE DRAWING

FIG. 1 is a graph of soluble Brimonidine tartrate verses pH at various carboxymethylcellulose concentrations.

DETAILED DESCRIPTION OF THE INVENTION

Compositions comprising TACs, SECs and oxy-chloro components are provided. The TACs in the present compositions are made more soluble and may be more effectively utilized as therapeutic agents. Suitable SECs for solubilizing TACs may be used concurrently with oxy-chloro components in the present compositions to increase the solubility of the TACs substantially without detrimentally affecting the preservative effectiveness of the oxy-chloro components. In other words, SECs employed in the present compositions may effectively increase the solubility of TACs without substantially interfering with the functions of other components in the compositions. The SECs employed in the present compositions may be effective in the solubilization of ionized TACs, unionized TACs or both.

Oxy-chloro components are included in the present compositions to assist in preserving the compositions. Particularly, the oxy-chloro components are not substantially detrimentally affected by the SECs present in the compositions. Moreover, the oxy-chloro components in the compositions are effective substantially without causing undue harm or irritation to the tissue to which the present compositions are administered.

The present compositions may, and preferably do, include liquid carrier components. For example, the components often have the characteristics of a liquid, for example, a liquid solution.

The presently useful TACs preferably are chosen to benefit from the presence of the SECs and the oxy-chloro components. In general, the TACs are provided with increased apparent solubility, preferably increased apparent water solubility, by the presence of the SECs.

Preferably, the TACs have increased solubility in the present compositions at pH's greater than 7, as compared to identical TACs, at comparable concentrations in similar compositions, without the SECs. More preferably, the TACs have increased solubility in the present compositions at pH's in the range of about 7 to about 10, as compared to TACs in similar compositions, at comparable concentrations, without the SECs.

Without wishing to be limited by any theory or mechanism of operation, it is believed that solubilized TACs are better able to cross the lipid membranes relative to unsolubilized TACs. It is further believed that the solubilized TACs are physically smaller and are therefore more able to physically permeate or diffuse through the lipid membranes.

In one embodiment, the SECs of this invention are capable of solubilizing the TACs in the environments into which they are introduced at therapeutically effective concentrations. Preferably, the biological environments into which the present compositions are introduced have pH's ranging from about 7 to about 9. For example, a composition comprising a SEC and a TAC may be administered to the cornea of a human eye, which has a pH of about 7, wherein the TAC is substantially solubilized at the administered area. Furthermore, in one embodiment, the TACs solubilized by SECs at the administered area diffuse through biological lipid membranes more readily than TACs which are not solubilized by SECs. The solubilization of TACs preferably reduces irritation to sensitive tissues in contact or interacting with the TACs.

Examples of the therapeutically active components which may be included in the present compositions include, but are not limited to, antibacterial substances such as beta-lactam antibiotics, such as cefoxitin, n-formamidoylthienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin and sulfonamides; aminoglycoside antibiotics such as gentamycin, kanamycin, amikacin, sisomicin and tobramycin; nalidixic acid and its analogs such as norfloxacin and the antimicrobial combination fluoroalanine/pentizidone, nitrofurazones and analogs thereof; antihistaminics and decongestants such as pyrilamine, chlorpheniramine, tetrahydrazoline, antazoline and analogs thereof; mast-cell inhibitors of histamine release, such as cromolyn; anti-inflammatories such as cortisone, hydrocortisone, hydrocortisone acetate, betamethasone, dexamethasone, dexamethasone sodium phosphate, prednisone, methylprednisolone, medrysone, fluorometholone, prednisolone, prednisolone sodium phosphate, triamcinolone, indainethacin, sulindac, its salts and its corresponding sulfides, and analogs thereof; miotics and anticholinergics such as echothiophate, pilocarpine, physostigmine salicylate, diisopropylfluorophosphate, epinephrine, dipivaloylepinephrine, neostigmine echothiopate iodide, demecarim bromide, carbamoyl choline chloride, methacholine, bethanechol, and analogs thereof; mydriatics such as atrophine, homatropine, scopolamine, hydroxyamphetamine, ephedrine, cocaine, tropicamide, phenylephrine, cyclopentolate, oxyphenonium, eucatropine; and the like and mixtures thereof.

Other TACs are: antiglaucama drugs, for example, timalol, and especially its maleic salt and R-timolol and a combination of timolol or R-timolol with pilocarpine; other adrenergic agonists and/or antagonists such as epinephrine and an epinephrine complex, or prodrugs such as bitartrate, borate, hydrochloride and dipivefrine derivatives; carbonic anhydrase inhibitors such as acetazolamide, dichlorphenamide, 2-(p-hydroxyphenyl)-thiothiophenesulfonamide, 6-hydroxy-2-benzothiazolesulfonamide, and 6-pivaloyloxy-2-benzothiazolesulfonamide; antiparasitic compounds and/or anti-protozoal compounds such as ivermectin, pyrimethamine, trisulfapidimidine, clindamycin and corticosteroid preparations; compounds having antiviral activity such as acyclovir, 5-iodo-2'-deoxyuridine (IDU), adenosine arabinoside (Ara-A), trifluorothymidine, interferon, and interferon-inducing agents such as poly I:C; antifungal agents such as amphotericin B, nystatin, flucytosine, natamycin and miconazole; anesthetic agents such as etidocaine cocaine, benoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine; ophthalmic diagnostic agents, such as: (a) those used to examine the retina such as sodium fluorescein, (b) those used to examine the conjunctiva, cornea and lacrimal apparatus, such as fluorescein and rose bengal and (c) those used to examine abnormal pupillary responses such as methacholine, cocaine, adrenaline, atropine, hydroxyamphetamine and pilocarpine; ophthalmic agents used as adjuncts in surgery, such as alpha-chymotrypsin and hyaluronidase; chelating agents such as ethylenediaminetetraacetic acid (EDTA) and deferoxamine; immunosuppressants and anti-metabolites such as methotrexate, cyclophosphamide, 6-mercaptopurine and azathioprine and combinations of the compounds mentioned above, such as antibiotics/antiinflammatories combinations such as the combination of neomycin sulfate and dexamethasone sodium phosphate and combinations concomitantly used for treating glaucoma, for example, a combination of timolol maleate and aceclidine; and the like and mixtures thereof.

In a preferred embodiment, the useful TACs include adrenergic agonists. The adrenergic agonists preferably are molecules containing amines. Also, the adrenergic agonists preferably are amine-containing molecules with pKa's of greater than 7, preferably about 7 to about 9.

More preferably, the useful TACs include alpha-adrenergic agonists. Examples of alpha-adrengergic agonists include, but not limited to, adrafinil, adrenolone, amidephrine, apraclonidine, budralazine, clonidine, cyclopentamine, detomidine, dimetofrine, dipivefrin, ephedrine, epinephrine, fenoxazoline, guanabenz, guanfacine, hydroxyamphetamine, ibopamine, indanazoline, isometheptene, mephentermine, metaraminol, methoxamine, methylhexaneamine, metizolene, midodrine, naphazoline, norepinephrine, norfenefrine, octodrine, octopamine, oxymetazoline, phenylephrine, phenylpropanolamine, phenylpropylmethylamine, pholedrine, propylhexedrine, pseudoephedrine, rilmenidine, synephrine, tetrahydrozoline, tiamenidine, tramazoline, tuaminoheptane, tymazoline, tyramine, xylometazoline, and the like and mixtures thereof.

In a still more preferred embodiment, the useful TACs include alpha-2-adrenergic agonists. As used herein, the term "alpha-2 adrenergic agonist" includes chemical entities, such as compounds, ions, complexes and the like, that produces a net sympatholytic response, resulting in increased accommodation, for example, by binding to presynaptic alpha-2 receptors on sympathetic postganglionic nerve endings or, for example, to postsynaptic alpha-2 receptors on smooth muscle cells. A sympatholytic response is characterized by the inhibition, diminishment, or prevention of the effects of impulses conveyed by the sympathetic nervous system. The alpha-2 adrenergic agonists of the invention bind to the alpha-2 adrenergic receptors presynaptically, causing negative feedback to decrease the release of neuronal norepinephrine. Additionally, they also work on alpha-2 adrenergic receptors postsynaptically, inhibiting beta-adrenergic receptor-stimulated formation of cyclic AMP, which contributes to the relaxation of the ciliary muscle, in addition to the effects of postsynaptic alpha-2 adrenergic receptors on other intracellular pathways. Activity at either pre- or postsynaptic alpha-2 adrenergic receptors will result in a decreased adrenergic influence. Decreased adrenergic influence results in increased contraction resulting from cholinergic innervations. Alpha-2 adrenergic agonists also include compounds that have neuroprotective activity. For example, 5-bromo-6-(2-imidozolin-2-ylamino) quinoxaline is an alpha-2-adrenergic agonist which has a neuroprotective activity through an unknown mechanism.

Without limiting the invention to the specific groups and compounds listed, the following is a list of representative alpha-2 adrenergic agonists useful in this invention: imino-imidazolines, including clonidine, apraclonidine; imidazolines, including naphazoline, xymetazoline, tetrahydrozoline, and tramazoline; imidazoles, including detomidine, medetomidine, and dexmedetomidine; azepines, including B-HT 920 (6-allyl-2-amino-5,6,7,8 tetrahydro-4H-thiazolo[4,5-d]-azepine and B-HT 933; thiazines, including xylazine; oxazolines, including rilmenidine; guanidines, including guanabenz and guanfacine; catecholamines and the like.

Particularly useful alpha-2-adrenergic agonists include quinoxaline components. In one embodiment, the quinoxaline components include quinoxaline, derivatives thereof and mixtures thereof. Preferably, the derivatives of quinoxaline include (2-imidozolin-2-ylamino) quinoxaline. More preferably, the derivatives of quinoxaline include 5-halide-6-(2-imidozolin-2-ylamino) quinoxaline. The "halide" of the 5-halide-6-(2-imidozolin-2-ylamino) quinoxaline may be a fluorine, a chlorine, an iodine, or preferably, a bromine, to form 5-bromo-6-(2-imidozolin-2-ylamino) quinoxaline. Even more preferably, the derivatives of quinoxaline to be used in accordance with this invention include a tartrate of 5-bromo-6-(2-imidozolin-2-ylamino) quinoxaline, or Brimonidine tartrate.

Other useful quinoxaline derivatives are well known. For example, useful derivatives of a quinoxaline include the ones disclose by Burke et al U.S. Pat. No. 5,703,077. See also Danielwicz et al 3,890,319. Each of the disclosures of Burke et al and Danielwicz et al is incorporated in its entirety by reference herein.

The quinoxaline and derivatives thereof, for example Brimonidine tartrate, are amine-containing and preferably have pKa's of greater than 7, preferably about 7.5 to 9.

Analogs of the foregoing compounds that function as alpha-2 adrenergic agonists also are specifically intended to be embraced by the invention.

Preferably, the alpha-2-adrenergic agonists, for example the ones listed above, are effective toward activating one or more of alpha-2A-adrenergic receptors, alpha-2B-adrenergic receptors and alpha-2D-adrenergic receptors.

Other useful TACs include ocular hypotensive agents (Woodward et al U.S. Pat. No. 5,688,819), cyclosporins (Ding et al U.S. Pat. No. 5,474,979), androgen tears (Sullivan U.S. Pat. No. 5,620,921), pyranoquinolinone derivatives (Cairns et al U.S. Pat. No. 4,474,787), compounds having retinoid-like activities (Chandraratna U.S. Pat. No. 5,089,509), ketorolac/pyrrole-1-carboxylic acids (Muchowski et al U.S. Pat. No. 4,089,969), ofloxacins/benzoxazine derivatives (Hayakawa et al U.S. Pat. No. 4,382,892), memantines (Lipton et al U.S. Pat. No. 5,922,773), RAR antagonists (Klein et al U.S. Pat. No. 5,952,345), RAR-alpha agonists (Teng et al U.S. Pat. No. 5,856,490). Each of the disclosures referred to in the above patents is incorporated in its entirety herein by reference.

In one embodiment, the TACs, for example Brimonidine tartrate, are substantially unionized in the composition. In another embodiment, the TACs are substantially unionized in the environment to which they are administered, for example the cornea of the human eye. Without wishing to be limited by any theory or mechanism of action, it is believed that the unionized forms of the TACs facilitate their permeation across membrane lipid bilayers.

Any suitable SEC, other than cyclodextrin, may be employed in accordance with the present invention. In one embodiment, the SECs include pyrrolinidone components. Examples of pyrrolinidone components are polyvinylpyrrolinidones, derivatives thereof and mixtures thereof. In a preferred embodiment, the SECs include polyanionic components. The useful polyanionic components include, but are not limited to, those materials which are effective in increasing the apparent solubility, preferably water solubility, of poorly soluble TACs and/or enhance the stability of the TACs and/or reduce unwanted side effects of the TACs. Furthermore, the polyanionic component is preferably ophthalmically acceptable at the concentrations used. Additionally, the polyanionic component preferably includes three (3) or more anionic (or negative) charges. In the event that the polyanionic component is a polymeric material, it is preferred that each of the repeating units of the polymeric material include a discrete anionic charge. Particularly useful anionic components are those which are water soluble, for example, soluble at the concentrations used in the presently useful liquid aqueous media, such as a liquid aqueous medium containing the polyanionic component and chlorite component.

The polyanionic component is preferably sufficiently anionic to interact with the TAC. Such interaction is believed to be desirable to solubilize the TAC and/or to maintain such TAC soluble in the carrier component, for example a liquid medium.

Polyanionic components also include one or more polymeric materials having multiple anionic charges. Examples include:

metal carboxymethylstarchs
metal carboxymethylhydroxyethylstarchs
hydrolyzed polyacrylamides and polyacrylonitriles
heparin
homopolymers and copolymers of one or more of:
   acrylic and methacrylic acids
   metal acrylates and methacrylates
   alginic acid
   metal alginates
   vinylsulfonic acid
   metal vinylsulfonate
   amino acids, such as aspartic acid, glutamic acid and the like
   metal salts of amino acids
   p-styrenesulfonic acid
   metal p-styrenesulfonate
   2-methacryloyloxyethylsulfonic acids metal 2-methacryloyloxethylsulfonates
3-methacryloyloxy-2-hydroxypropylsulonic acids
metal 3-methacryloyloxy-2-hydroxypropylsulfonates
2-acrylamido-2-methylpropanesulfonic acids
metal 2-acrylamido-2-methylpropanesulfonates
allylsulfonic acid
metal allylsulfonate and the like.

In one embodiment, the polyanionic components include anionic polysaccharides, other than cyclodextrins, which tend to exist in ionized forms at higher pH's, for example, pH's of about 7 or higher. The following are some examples of anionic polysaccharides which may be employed in accordance with this invention.

Polydextrose is a randomly bonded condensation polymer of dextrose which is only partially metabolized by mammals. The polymer can contain a minor amount of bound sorbitol, citric acid, and glucose.

Chondroitin sulfate also known as sodium chondroitin sulfate is a mucopolysaccharide found in every part of human tissue, specifically cartilage, bones, tendons, ligaments, and vascular walls. This polysaccharide has been extracted and purified from the cartilage of sharks.

Carrageenan is a linear polysaccharide having repeating galactose units and 3,6 anhydrogalactose units, both of which can be sulfated or nonsulfated, joined by alternating 1–3 and beta 1–4 glycosidic linkages. Carrageenan is a hydrocolloid which is heat extracted from several species of red seaweed and irish moss.

Maltodextrins are water soluble glucose polymers which are formed by the reaction of starch with an acid and/or enzymes in the presence of water.

Other polysaccharides found useful in the present invention are hydrophilic colloidal materials and include the natural gums such as gellan gum, alginate gums, i.e., the ammonium and alkali metal salts of alginic acid and mixtures thereof. In addition, chitosan, which is the common name for deacetylated chitin is useful. Chitin is a natural product comprising poly-(N-acetyl-D-glucosamine). Gellan gum is produced from the fermentation of pseudomonas elodea to yield an extracellular heteropolysaccharide. The alginates and chitosan are available as dry powders from Protan, Inc., Commack, N.Y. Gellan gum is available from the Kelco Division of Merk & Co., Inc., San Diego, Calif.

Generally, the alginates can be any of the water-soluble alginates including the alkali metal alginates, such as sodium, potassium, lithium, rubidium and cesium salts of alginic acid, as well as the ammonium salt, and the soluble alginates of an organic base such as mono-, di-, or tri-ethanolamine alginates, aniline alginates, and the like. Generally, about 0.2% to about 1% by weight and, preferably, about 0.5% to about 3.0% by weight of gellan, alginate or chitosan ionic polysaccharides, based upon the total weight of the composition, are used to obtain the gel compositions of the invention.

A particularly useful class of polyanionic component includes anionic cellulose derivatives. Anionic cellulose derivatives include metal carboxymethylcelluloses, metal carboxymethylhydroxyethylcelluloses and hydroxypropylmethylcelluloses and derivatives thereof.

The present polyanionic components often can exist in the unionized state, for example, in the solid state, in combination with a companion or counter ion, in particular a plurality of discrete cations equal in number to the number of discrete anionic charges so that the unionized polyanionic component is electrically neutral. For example, the present unionized polyanionic components may be present in the acid form and/or in combination with one or more metals.

Since the polyanionic components are preferably ophthalmically acceptable, it is preferred that the metal associated with the unionized polyanionic component be ophthalmically acceptable in the concentrations used. Particularly useful metals include the alkali metals, for example, sodium and potassium, the alkaline earth metals, for example, calcium and magnesium, and mixtures thereof. Sodium is very useful to provide the counter ion in the unionized polyanionic component. Polyanionic components which, in the unionized states, are combined with cations other than H+ and metal cations can be employed in the present invention.

In a preferred embodiment, the polyanionic polymers are cyclized. More preferably, the cyclized anionic polymers include less than ten monomer units. Even more preferably, the cyclized polyanionic polymers include less than six monomer units.

The amount of SEC in the present compositions is not of critical importance so long as solubility at the alpha-2-adrenergic agonist component is at least somewhat increased and is present in a biologically acceptable amount. Such amount should be effective to perform the desired function or functions in the present composition and/or after administration to the human or animal. In one embodiment, the amount of SEC, preferably the polyanionic component, is sufficient to complex at least in a major amount, and more preferably substantially all, of the TAC in the present composition. In one useful embodiment, the amount of polyanionic component in the present composition is in the range of about 0.1% to about 30% (w/v) or more of the composition. Preferably, the amount of polyanionic component is in the range of about 0.2% (w/v) to about 10% (w/v). More preferably, the amount of polyanionic component is in the range of about 0.2% (w/v) to about 0.6% (w/v). Even more preferably, the polyanionic component is carboxymethylcellulose and is present in the composition in the range of about 0.2% (w/v) to about 0.6% (w/v). A particularly useful concentration of carboxymethylcellulose in the present composition is about 0.5%.

In one embodiment, carboxymethylcellulose may help solubilize ionized TACs. In another embodiment, carboxymethylcellulose may help solubilize unionized TACs. In a preferred embodiment, the carboxylmethylcellulose help solubilize ionized Brimonidine tartrate. More preferably, the carboxylmethylcellulose helps solubilize unionized Brimonidine tartrate.

In one broad embodiment, the preservative components are selected so as to be effective and efficacious as preservatives in the present compositions, that is in the presence of SECs, and preferably have reduced toxicity and more preferably substantially no toxicity when the compositions are administered to a human or animal.

Preservatives which are commonly used in pharmaceutical compositions are often less effective when used in the presence of solubilizing agents. In certain instances, this reduced preservative efficacy can be compensated for by using increased amounts of the preservative. However, where sensitive or delicate body tissue is involved, this approach may not be available since the preservative itself may cause some adverse reaction or sensitivity in the human or animal, to whom the composition is administered.

Preferably, the present preservative components or components effective in aiding to preserve the compositions are effective in concentrations of less than about 1% (w/v) or about 0.8% (w/v) and may be 500 ppm (w/v) or less, for example, in the range of about 10 ppm (w/v) or less to about 200 ppm (w/v). Preservative components or components effective in aiding to preserve the compositions in accordance with the present invention preferably include, but are not limited to, those which form complexes with the polyanionic component to a lesser extent than does benzalkonium chloride.

Examples of the components effective in aiding to preserve the compositions, preferably the TACs therein, include, but are not limited to, oxidative preservative components, for example oxy-chloro components, peroxides, persalts, peracids, and the like, and mixtures thereof. Specific examples of oxy-chloro components useful as preservatives in accordance with the present invention include hypochlorite components, for example hypochlorites; chlorate components, for example chlorates; perchlorate components, for example perchlorates; and chlorite components. Examples of chlorite components include stabilized chlorine dioxide (SCD), metal chlorites, such as alkali metal and alkaline earth metal chlorites, and the like and mixtures therefor. Technical grade (or USP grade) sodium chlorite is a very useful preservative component. The exact chemical composition of many chlorite components, for example, SCD, is not completely understood. The manufacture or production of certain chlorite components is described in McNicholas U.S. Pat. No. 3,278,447, which is incorporated in its entirety herein by reference. Specific examples of useful SCD products include that sold under the trademark Dura Klor by Rio Linda Chemical Company, Inc., and that sold under the trademark Anthium Dioxide by International Dioxide, Inc. An especially useful SCD is a product sold under the trademark Purite® by Allergan, Inc. Other examples of oxidative preservative components includes peroxy components. For example, trace amounts of peroxy components stabilized with a hydrogen peroxide stabilizer, such as diethylene triamine penta(methylene phosphonic acid) or 1-hydroxyethylidene-1,1-diphosphonic acid, may be utilized as a preservative for use in components designed to be used in the ocular environment. Also, virtually any peroxy component may be used so long as it is hydrolyzed in water to produce hydrogen peroxide. Examples of such sources of hydrogen peroxide, which provide an effective resultant amount of hydrogen peroxide, include sodium perborate decahydrate, sodium peroxide and urea peroxide. It has been found that peracetic acid, an organic peroxy compound, may not be stabilized utilizing the present system. See, for example, Martin et al U.S. Pat. No. 5,725,887, the disclosure of which is incorporated in its entirety herein by reference.

In a broad embodiment of the invention, additional preservatives other than oxidative preservative components may be included in the compositions. The choice of preservatives may depend on the route of administration. Preservatives suitable for compositions to be administered by one route may possess detrimental properties which preclude their administration by another route. For nasal and ophthalmic compositions, preferred preservatives include quaternary ammonium compounds, in particular the mixture of alkyl benzyl dimethyl ammonium compounds and the like known generically as "benzalkonium chloride." For compositions to be administered by inhalation, however, the preferred preservative is chlorbutol and the like. Other preservatives which may be used, especially for compositions to be administered rectally, include alkyl esters of p-hydroxybenzoic acid and the like and mixtures thereof, such as the mixture of methyl, ethyl, propyl and butyl esters which is sold under the trade name "Nipastat."

In another broad aspect of the present invention, compositions are provided which comprise a TAC, a preservative component in an effective amount to at least aid in preserving, preferably in an amount effective to preserve, the compositions and a liquid carrier component. Preferably, the preservative components include oxy-chloro components, such as compounds, ions, complexes and the like which (1) do not substantially or significantly detrimentally affect the TACs in the compositions or the patients to whom the compositions are administered, and (2) are substantially biologically acceptable and chemically stable. Such compositions in accordance with the present invention comprise a TAC, an oxy-chloro component, and a liquid carrier component, and preferably are substantially free of cyclodextrins.

The carrier components useful in the present invention are selected to be non-toxic and have no substantial detrimental effect on the present compositions, on the use of the compositions or on the human or animal to whom the compositions are administered. In one embodiment, the carrier component is a liquid carrier. In a preferred embodiment, the carrier component is a liquid aqueous carrier component. A particularly useful aqueous liquid carrier component is that derived from saline, for example, a conventional saline solution or a conventional buffered saline solution. The aqueous liquid carrier preferably has a pH in the range of about 6 to about 9 or about 10, more preferably about 6 to about 8, and still more preferably about 7.5. The liquid medium preferably has an ophthalmically acceptable tonicity level, for example, of at least about 200 mOsmol/kg, more preferably in the range of about 200 to about 400 mOsmol/kg. In an especially useful embodiment, the osmolality or tonicity of the carrier components substantially correspond to the tonicity of the fluids of the eye, in particular the human eye.

In one embodiment, the carrier components containing the TACs, SECs and preservatives may have viscosities of more than about 0.01 centipoise (cps) at 25° C., preferably more than about 1 cps, even more preferably more than about 10 cps at 25° C. In a preferred embodiment, the composition has a viscosity of about 50 cps at 25° C. and comprises a conventional buffer saline solution, a carboxymethylcellulose and a Brimonidine tartrate.

In order to insure that the pH of the aqueous liquid carrier component, and thus the pH of the composition, is maintained within the desired range, the aqueous liquid carrier component may include at least one buffer component. Although any suitable buffer component may be employed, it is preferred to select such component so as not to produce a significant amount of chlorine dioxide or evolve significant amounts of gas, such as $CO_2$. It is preferred that the buffer component be inorganic. Alkali metal and alkaline earth metal buffer components are advantageously used in the present invention.

Any suitable ophthalmically acceptable tonicity component or components may be employed, provided that such component or components are compatible with the other ingredients of the liquid aqueous carrier component and do not have deleterious or toxic properties which could harm the human or animal to whom the present compositions are administered. Examples of useful tonicity components include sodium chloride, potassium chloride, mannitol, dextrose, glycerin, propylene glycol and mixtures thereof. In one embodiment, the tonicity component is selected from inorganic salts and mixtures thereof.

The present compositions may conveniently be presented as solutions or suspensions in aqueous liquids or non-aqueous liquids, or as oil-in-water or water-in-oil liquid emulsions. The present compositions may include one or more additional ingredients such as diluents, flavoring agents, surface active agents, thickeners, lubricants, and the like, for example, such additional ingredients which are conventionally employed in compositions of the same general type.

The present compositions in the form of aqueous suspensions may include excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gun tragacanth and gun acacia; dispersing or wetting agents may be a naturally occurring phosphatide, for example, lecithin, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example, polyoxyethylene sorbitan mono-oleate, and the like and mixtures thereof. Such aqueous suspensions may also contain one or more coloring agents, one or more flavoring agents and one or more sweetening agents, such as sucrose, saccharin, and the like and mixtures thereof.

The present compositions in the form of oily suspensions may be formulated in a vegetable oil, for example, olive oil, sesame oil or coconut oil, or in a mineral oil such as liquid paraffin. Such suspensions may contain a thickening agent, for example beeswax, hard paraffin or cetyl alcohol. Sweetening agents, such as those set forth above, and flavoring agents may be added to provide a palatable oral preparation.

The present compositions may also be in the form of oil-in-water emulsions. The oily phase may be a vegetable oil, for example, olive oil or arachis oil, or a mineral oil, for example, liquid paraffin, and the like and mixtures thereof. Suitable emulsifying agents may be naturally-occurring gums, for example, gum acacia or gun tragacanth, naturally-occurring phosphatides, for example, soya bean lecithin, and esters or partial esters derived from fatty acids and hexitol anhydrides, for example, sorbitan mono-oleate, and condensation products of the said partial esters with ethylene oxide, for example, polyoxyethylene sorbitan mono-oleate. The emulsions may also contain sweetening and flavoring agents.

The present compositions in the form of syrups and elixirs may be formulated with sweetening agents, for example, as described elsewhere herein. Such formulations may also contain a demulcent, and flavoring and coloring agents.

The specific dose level for any particular human or animal depends upon a variety of factors including the activity of the active component employed, the age, body weight, general health, sex, diet, time of administration, route of administration, rate of excretion, drug combination and the severity of the particular condition undergoing therapy.

The following non-limiting examples illustrate certain aspects of the present invention.

EXAMPLE 1

Brimonidine tartrate has a pKa of about 7.78. The pH-solubility profile of 0.5% (w/v) Brimonidine tartrate in a formulation, Ophthalmic Solution, was established in the pH range of about 5 to about 8 at 23° C. Table 1. It will be understood that concentrations of adrenergic agonists other than 0.5% may be used, so long as they have therapeutic activity. Likewise, the temperature may be varied, for example, solubility curves may be performed at 37° C. (98.6° F.). The formulation vehicle was prepared by first dissolving polyvinyl alcohol (PVA) in water. The PVA was added to approximately ⅓ of the required total amount of purified water with constant stirring. The slurry was stirred for 20–30 minutes and then heated to 80–95° C. with constant stirring. The mixture was removed from the heat source within 1 hour after having reached the temperature of 80–90° C. and stirred for an additional 10 minutes to ensure homogeneity (Part I). The other ingredients of the Ophthalmic Solution, except for Brimonidine tartrate, were dissolved in a separate container with an additional ⅓ of the required total amount of purified water (Part II). The PVA mixture (Part I) was then quantitatively transferred to Part II using several rinse volumes of purified water. The solution was adjusted to final volume with purified water without pH adjustment.

Brimonidine tartrate was weighed and transferred to a 10 mL test tube containing 5 mL of the formulation vehicle described above. The pH of each sample was then adjusted to a desired value using dilute sodium hydroxide and/or dilute hydrochloric acid. The samples were placed in a rack on a stir plate and stirred at high speed to achieve uniform mixing for 2 days; a partition was placed between the rack and the stir plate to prevent any heat diffusion from the stir plate to the samples. The temperature of the laboratory was monitored throughout the study and was found to be 23±1° C.

At the end of two days of stirring, the pH value of each sample was measured, and then approximately 1 mL of each sample was placed in a micro centrifuge tube (polypropylene) and centrifuged at 4,000 rpm for 10 minutes. The supernatant was filtered through a 1 $\mu$m filter unit (Whatman, 13 mm, PTFE). The first 3–4 drops of the filtrate were discarded; the rest of the filtrate was received and diluted quantitatively with HPLC mobile phase. The dilute sample was then injected directly on the HPLC column (Dupont Zorbax, 250 mm×4.6 mm, 5$\mu$m) for Brimonidine tartrate assay in order to quantify the amount of Brimonidine tartrate. A control of 10.05% Brimonidine tartrate was prepared in the formulation vehicle at pH 6.3–6.5 and assayed before (untreated) and after (treated) centrifugation and filtration. This was done to evaluate the potential loss of Brimonidine tartrate in these two steps of the sample preparation. To ensure reproducibility, the study was repeated on consecutive days.

TABLE I

| 0.5% Brimonidine tartrate in Ophthalmic Solution. | |
|---|---|
| Ingredient | Percent (w/v) |
| Brimonidine tartrate | 0.50 |
| Benzalkonium Chloride, NF | 0.0050 |
| Polyvinyl Alcohol, USP | 1.4 |
| Sodium Chloride, USP | 0.66 |
| Sodium Citrate, Dihydrate, USP | 0.45 |
| Hydrochloric Acid, NF or Sodium Hydroxide, NF for pH adjustment | 5–8 |
| Purified Water, USP | QS |

The solubility data for Brimonidine tartrate in the formulation vehicles are presented in Table II. The results show that the solubility of Brimonidine tartrate is highly pH-dependent and spans more than two orders of magnitude over the pH range of 5–8. The solubility decreases sharply as the pH increases. The results for the treated and untreated controls are very close, suggesting that centrifugation and filtration does not cause any significant loss of Brimonidine tartrate. The two solubility profiles obtained on consecutive days agree with each other.

TABLE II

Solubility of Brimonidine tartrate in the Ophthalmic Solution Over pH Range of 5 to 8.

| Sample | STUDY 1 | | STUDY 2 | |
| --- | --- | --- | --- | --- |
| | pH[a] | Solubility[e] | pH[a] | Solubility[e] |
| 1 | 5.55 | ≦164.4[b] | 5.50 | ≦200.6[b] |
| 2 | 5.92 | 132.6 | 5.92 | 160.8 |
| 3 | 6.14 | 30.4 | 6.06 | 50.1 |
| 4 | 6.57 | 7.55 | 6.90 | 3.19 |
| 5 | 7.00 | 2.69 | 7.40 | 1.19 |
| 6 | 7.45 | 1.17 | 7.77 | 0.63 |
| 7 | 7.83 | 0.62 | 7.86 | 0.58 |
| 8 | — | — | 7.88 | 0.54 |
| Control/ (untreated) | — | 0.486[c] | — | — |
| Control/ (treated) | — | 0.484[d] | — | — |

[a]Measured after stirring for two-days before sample withdrawal for centrifugation and filtration.
[b]Represents theoretical concentration based on sample weight. The sample solution was clear indicating that all of the Brimonidine tartrate had dissolved.
[c]Concentration of Brimonidine tartrate in control before centrifugation and filtration step.
[d]Concentration of Brimonidine tartrate in control after centrifugation and filtration step.
[e]% w/v.

EXAMPLE 2

The pH-solubility profiles of Brimonidine tartrate in compositions (solutions) containing SECs and oxy-chloro components were determined. Particularly, the effects of sodium carboxymethylcellulose (CMC), an SEC, on the solubility of Brimonidine tartrate at various pH conditions were determined. The various concentrations of CMC tested with Brimonidine tartrate were 0%, 0.056%, 0.17%, 0.5%, 1.5% (w/v), Table III.

The samples tested also contained isotonic components, buffer components, and stabilized chlorine dioxide (Purite™), Table III. Sodium carboxymethyl-cellulose, sodium chloride, potassium chloride, calcium chloride dihydrate, and magnesium chloride hexahydrate were USP grade. Boric acid and sodium borate decahydrate were NF grade.

TABLE III

| | Sample 1 | Sample 2 | Sample 3 | Sample 4 | Sample 5 |
| --- | --- | --- | --- | --- | --- |
| Brimonidine tartrate | 0.2% | 0.2% | 0.2% | 0.2% | 0.2% (w/v) |
| CMC | 0.0% | 0.056% | 0.17% | 0.5% | 1.5% (w/v) |
| Stabilized chlorine dioxide[a] | 0.005% | 0.005% | 0.005% | 0.005% | 0.005% (w/v) |
| Sodium chloride | 0.58% | 0.58% | 0.58% | 0.58% | 0.58% (w/v) |
| Potassium chloride | 0.14% | 0.14% | 0.14% | 0.14% | 0.14% (w/v) |
| Calcium chloride, dihydrate | 0.02% | 0.02% | 0.02% | 0.02% | 0.02% (w/v) |
| magnesium chloride, hexahydrate | 0.006% | 0.006% | 0.006% | 0.006% | 0.006% (w/v) |
| boric acid | 0.2% | 0.2% | 0.2% | 0.2% | 0.2% (w/v) |
| sodium tetraborate, decahydrate | 0.14% | 0.14% | 0.14% | 0.14% | 0.14% (w/v) |

[a]Sold under the trademark Purite ™ by Allergan, Inc.

Each sample (1 through 5) was subjected to a range of pH's from about 7 to about 10. The vials containing the sample solutions were placed on a laboratory rotator and left for equilibration for fifteen days at room temperature (~21° C.). The sample solutions were filtered using a 25 mm diameter polysulfone cellulose acetate syringe type filter with 0.45 μm pore size. The filtered solutions were assayed for Brimonidine.

Conventional HPLC and detection techniques were used to detect and determine the concentrations of soluble Brimonidine tartrate. Table IV. The solubility is plotted against pH for each CMC concentration. The experimental data points were fitted to a modified Henderson-Hasselbalch equation using a nonlinear least squares routine (Deltagraph version 4.0 DeltaPoint, Inc.), FIG. 1. The $R^2$ values show the goodness of fit between the experimental values and the theoretical equation to be better than 0.991.

TABLE IV

Solubility of Brimonidine tartrate (%)

| pH | 0% CMC | 0.056% CMC | 0.17% CMC | 0.5% CMC | 1.5% CMC |
| --- | --- | --- | --- | --- | --- |
| 6.67 | | 0.9302 | | 1.4464 | |
| 6.68 | 1.4256 | | 1.4200 | | |
| 6.93 | | | 0.7302 | | |
| 7.10 | | | | 0.3693 | |
| 7.11 | 0.2064 | 0.2828 | | | |
| 7.35 | | | | | 0.1904 |
| 7.56 | | | | 0.1451 | |
| 7.68 | 0.0786 | | | | |
| 7.77 | | 0.0721 | | | |
| 7.81 | | | 0.0735 | | |
| 8.10 | | | | | 0.0498 |
| 8.46 | | | | 0.0313 | |
| 8.50 | 0.0286 | | | | |
| 8.55 | | | 0.0328 | | |
| 8.67 | | | | | 0.0311 |
| 9.93 | | 0.0234 | | | |
| 9.94 | | | | 0.0250 | |
| 10.05 | | | 0.0241 | | |
| 10.09 | 0.0218 | | | | |
| 10.11 | | | | | 0.0222 |

FIG. 1 clearly shows that the solubility of Brimonidine tartrate tends to increase with increasing CMC concentrations. For example, at pH 7.5, the sample with 0% CMC resulted in 1000 ppm of Brimonidine tartrate; 0.056% CMC, 1300 ppm; 0.17% CMC, 1300 ppm; and 0.5%, 1600 ppm. At pH 7.5, the sample with 1.5% CMC resulted in about 1400 ppm, which is less than that of a similar solution with CMC at 0.5%. It is unclear at this point what the cause of this observation may be. Nonetheless, Brimonidine tartrate is more soluble in solution with a 1.5% CMC than with no CMC.

CMC is also effective to solubilize Brimonidine tartrate in a biological environment, for example the biological environment of the cornea.

While this invention has been described with respect to various specific examples and embodiments, it is to be understood that the invention is not limited thereto and that it can be variously practiced with the scope of the following claims.

What is claimed is:

1. A composition comprising:
    a therapeutically active component selected from the group consisting of alpha-2-adrenergic agonists and mixtures thereof, and being present in an amount effective to provide a desired therapeutic benefit to a patient to whom the composition is administered;
    a solubility enhancing component, other than a cyclodextrin, in an amount effective to increase the solubility of the therapeutically active component in the composition relative to the solubility of an identical therapeutically active component in a similar composition without the solubility enhancing component;
    an oxy-chloro component in an effective amount to at least aid in preserving the composition; and
    a liquid carrier component.

2. The composition of claim 1 wherein the therapeutically active component is selected from the group consisting of imino-imidazolines, imidazolines, imidazoles, azepines, thiazines, oxazolines, guanidines, catecholamines, and mixtures thereof.

3. The composition of claim 1 wherein the therapeutically active component includes a quinoxaline component.

4. The composition of claim 3 wherein the quinoxaline component is selected from the group consisting of quinoxalines, quinoxaline derivatives, and mixtures thereof.

5. The composition of claim 3 wherein the quinoxaline component is selected from the group consisting of quinoxaline, (2-imidozolin-2-ylamino) quinoxaline, 5-bromo-6-(2-imidozolin-2-ylamino) quinoxaline, and tartrate of 5-bromo-6-(2-imidozolin-2-ylamino) quinoxaline, and mixtures thereof.

6. The composition of claim 1 wherein the therapeutically active component comprises a tartrate of 5-bromo-6-(2-imidozolin-2-ylamino) quinoxaline.

7. The composition of claim 1 wherein the therapeutically active component has increased diffusion through a lipid membrane relative to an identical therapeutically active component in a similar composition without the solubility enhancing component.

8. The composition of claim 1 wherein the solubility enhancing component is effective to increase the solubility in a biological environment of the therapeutically active component relative to the solubility in a biological environment of an identical therapeutically active component in a similar composition without the solubility enhancing component.

9. The composition of claim 1 wherein the solubility enhancing component comprises a polyanionic component.

10. The composition of claim 9 wherein said polyanionic components is selected from the group consisting of anionic cellulose derivatives, anionic polymers derived from acrylic acid, anionic polymers derived from methacrylic acid, anionic polymers derived from alginic acid, anionic polymers derived from amino acids and mixtures thereof.

11. The composition of claim 1 wherein the solubility enhancing component comprises an anionic cellulose derivative.

12. The composition of claim 1 wherein the solubility enhancing component comprises a carboxymethylcellulose.

13. The composition of claim 1 wherein the solubility enhancing component is present in an amount in a range of about 0.1% (w/v) to about 30% (w/v).

14. The composition of claim 1 wherein the solubility enhancing component is present in an amount in a range of about 0.2% (w/v) to about 10 (w/v).

15. The composition of claim 1 wherein the solubility enhancing component is present in an amount in a range of about 0.2% (w/v) to about 0.6% (w/v).

16. The composition of claim 1 wherein the oxy-chloro component is selected from the group consisting of hypochlorite components, perchlorate components, chlorite components and mixtures thereof.

17. The composition of claim 1 wherein the oxy-chloro component comprises a chlorite component.

18. The composition of claim 1 wherein the oxy-chloro component comprises stabilized chlorine dioxide.

19. The composition of claim 1, wherein the oxy-chloro component is present in an amount of about 500 ppm (w/v) or less.

20. The composition of claim 1 wherein the oxy-chloro component is present in an amount in a range of about 10 ppm (w/v) to about 200 ppm (w/v).

21. The composition of claim 1 which further comprises an additional preservative component other than the oxy-chloro component in an amount effective to at least aid in preserving the composition.

22. The composition of claim 21, wherein the additional preservative component is selected from the group consisting of sorbic acid, benzalkonium chloride, chlorbutol and alkyl esters of p-hydroxybenzoic acid and mixtures thereof.

23. The composition of claim 1 wherein the liquid carrier is an aqueous liquid carrier component.

24. The composition of claim 1 which is a solution.

25. The composition of claim 1 which has a pH of about 7 or greater.

26. The composition of claim 1 which has a pH in a range of about 7 to about 9.

27. The composition of claim 1 which is ophthalmically acceptable.

28. A composition comprising:
    a therapeutically active component selected from the group consisting of alpha-2-adrenergic agonists and mixtures thereof in an amount effective to provide a therapeutic benefit to a patient to whom the composition is administered;
    an anionic cellulose derivative in an amount effective to increase the solubility of the therapeutically active component;
    a chlorite component in an effective amount to at least aid in preserving the composition; and
    an aqueous liquid carrier component.

29. The composition of claim 28 wherein the therapeutically active component comprises a tartrate of 5-bromo-6-(2-imidozolin-2-ylamino) quinoxaline.

30. The composition of claim 28 wherein the anionic cellulose derivative comprises carboxymethylcellulose.

31. The composition of claim 28 wherein the anionic cellulose derivative is present in an amount in a range of about 0.2% to about 0.6% (w/v).

32. A composition comprising:
    a tartrate of 5-bromo-6-(2-imidozolin-2-ylamino) quinoxaline in an amount effective to provide a therapeutic benefit to a patient to whom the composition is administered;
    a solubility enhancing component in an amount effective to increase the solubility of the tartrate of 5-bromo-6-(2-imidozolin-2-ylamino) quinoxaline;
    a chlorite component in an effective amount to at least aid in preserving the composition; and
    an aqueous liquid carrier component.

33. The composition of claim 32 wherein the solubility enhancing component comprises a carboxymethylcellulose.

34. The composition of claim 32 which is ophthalmically acceptable.

35. A composition comprising:
a therapeutically active component in an amount effective to provide a desired therapeutic benefit to a patient to whom the composition is administered;
an oxy-chloro component in an effective amount to at least aid in preserving the composition; and
a liquid carrier component, wherein the composition is substantially free of cyclodextrins.

36. The composition of claim 35 wherein the therapeutically active component is selected from the group consisting of antibacterials, antihistamines, decongestants, antiinflammatories, antiparasitics, miotics, anticholinergics, adrenergics, antivirals, local anesthetics, antifungals, amoebicidals, trichomonocidals, analgesics, mydriatics, antiglaucoma drugs, carbonic anhydrase inhibitors, ophthalmic diagnostic agents, ophthalmic agents used as adjuvants in surgery, chelating agents, antineoplascics, antihypertensives, muscle relaxants, diagnostics, and mixtures thereof.

37. The composition of claim 35 wherein the therapeutically active component is selected from the group consisting of adrenergic agonists and mixtures thereof.

38. The composition of claim 35 wherein the therapeutically active component is selected from the group consisting of alpha-2-adrenergic agonists and mixtures thereof.

39. The composition of claim 35 wherein the therapeutically active component is selected from the group consisting of imino-imidazolines, imidazolines, imidazoleS, azepines, thiazines, oxazolines, guanidines, catecholamines, and mixtures thereof.

40. The composition of claim 35 wherein the therapeutically active component includes a quinoxaline component.

41. The composition of claim 40 wherein the quinoxaline component is selected from the group consisting of quinoxalines, quinoxaline derivatives, and mixtures thereof.

42. The composition of claim 40 wherein the quinoxaline component is selected from the group consisting of quinoxaline, (2-imidozolin-2-ylamino) quinoxaline, 5-bromo-6-(2-imidozolin-2-ylamino) quinoxaline, and tartrate of 5-bromo-6-(2-imidozolin-2-ylamino) quinoxaline, and mixtures thereof.

43. The composition of claim 35 wherein the therapeutically active component comprises a tartrate of 5-bromo-6-(2-imidozolin-2-ylamino) quinoxaline.

44. The composition of claim 35, which further includes a solubility enhancing component, other than a cyclodextrin, in an amount effective to increase the solubility of the therapeutically active component in the composition relative to the solubility of an identical therapeutically active component in a similar composition without the solubility enhancing component.

45. The composition of claim 44 wherein the solubility enhancing component comprises a polyanionic component.

46. The composition of claim 35 wherein the oxy-chloro component is selected from the group consisting of hypochlorite components, perchlorate components, chlorite components and mixtures thereof.

47. The composition of claim 35 wherein the oxy-chloro component comprises a chlorite component.

48. The composition of claim 35 wherein the oxy-chloro component comprises stabilized chlorine dioxide.

49. The composition of claim 35 which is ophthalmically acceptable.

* * * * *